United States Patent [19]

Opp

[11] Patent Number: 4,471,055
[45] Date of Patent: Sep. 11, 1984

[54] PROCESS AND KIT FOR DETERMINING CONCENTRATIONS OF ALDEHYDES

[75] Inventor: Charles W. Opp, Cottage Grove, Minn.

[73] Assignee: Minnesota Mining and Manufacturing Company, St. Paul, Minn.

[21] Appl. No.: 362,303

[22] Filed: Mar. 26, 1982

[51] Int. Cl.³ .......................................... G01N 21/78
[52] U.S. Cl. .................................... 436/128; 422/56; 422/61; 436/166
[58] Field of Search ........................... 422/56, 57, 61; 436/130, 128, 164, 166, 169, 170, 95

[56] References Cited

U.S. PATENT DOCUMENTS

| | | | |
|---|---|---|---|
| D. 250,599 | 12/1978 | Amand | D24/63 X |
| 2,908,555 | 10/1959 | Grosskopf | 436/130 X |
| 3,006,735 | 10/1961 | Jordan | 23/230 R |
| 3,008,879 | 11/1961 | Harvill | 195/103.5 |
| 3,409,405 | 11/1968 | Mohan et al. | 23/230 |
| 3,661,717 | 5/1972 | Nelson | 435/296 X |
| 3,723,064 | 3/1973 | Liotta | 422/56 X |
| 3,837,809 | 9/1974 | Chapman | 22/253 TP |
| 3,964,871 | 6/1976 | Hochstrasser | 23/253 TP |
| 4,036,589 | 7/1977 | King | 23/230 B |
| 4,129,417 | 12/1978 | White | 23/230 B |
| 4,298,569 | 11/1981 | Read | 422/27 |
| 4,349,352 | 9/1982 | Manning et al. | 436/67 |
| 4,380,587 | 4/1983 | Koocher | 436/128 |

FOREIGN PATENT DOCUMENTS

| | | |
|---|---|---|
| 2809475 | 8/1979 | Fed. Rep. of Germany . |
| 24877 | 10/1969 | Japan .................. 436/128 |
| 2085583 | 9/1981 | United Kingdom . |

OTHER PUBLICATIONS

Jacobson et al., 46 Analytical Chemistry 298 (1974).
Surgikos Data Sheet entitled "*Exclusive Breakthrough in Disinfection*".

Primary Examiner—Arnold Turk
Attorney, Agent, or Firm—Donald M. Sell; James A. Smith; Robert W. Sprague

[57] ABSTRACT

A process and kit which are useful in determining whether the concentration of an aldehyde in a sample is in excess of a predetermined concentration. Two reaction systems are employed. The first reaction system acts first in transforming quantitatively to a first reaction product the amount of aldehyde equal to the predetermined concentration. The second reaction system then acts to transform any remaining aldehyde to a second reaction product which is detectable visually. In a preferred embodiment, delay in action of the second reaction system is achieved by formulating a reactant for the second reaction system in tablet form. Such tablets are also described herein.

23 Claims, 3 Drawing Figures

U.S. Patent  Sep. 11, 1984  4,471,055
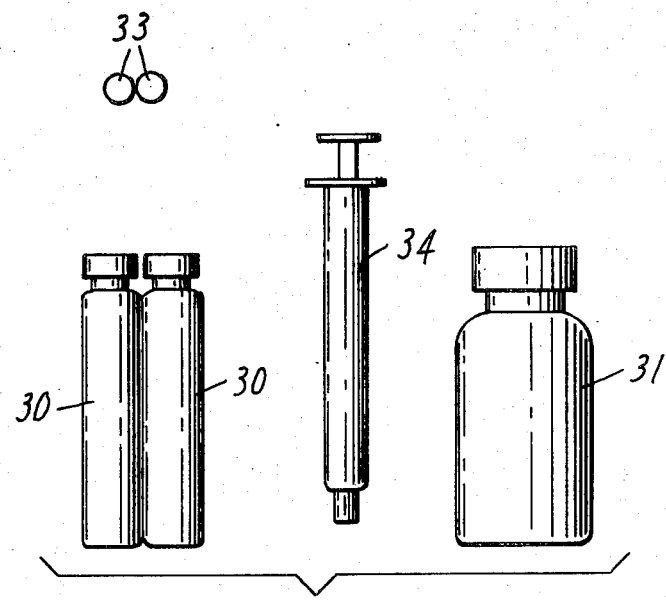
FIG. 3
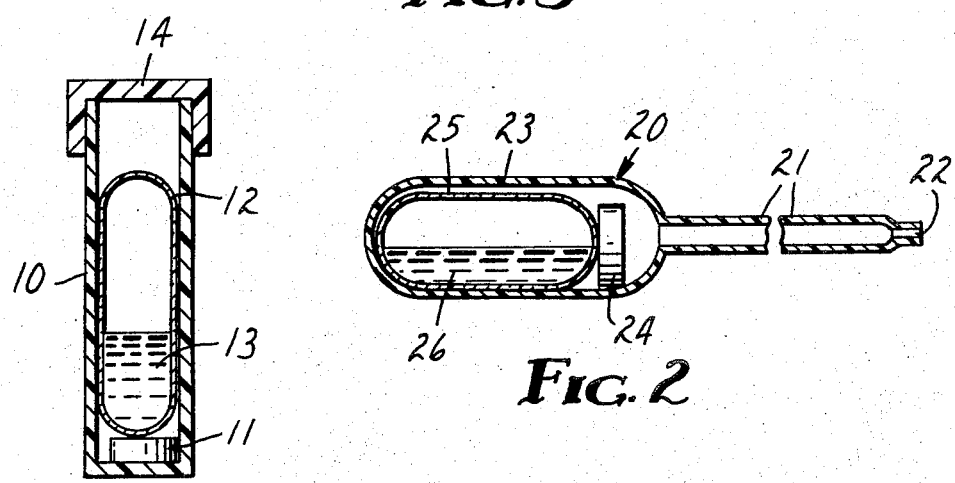
FIG. 1
FIG. 2

PROCESS AND KIT FOR DETERMINING CONCENTRATIONS OF ALDEHYDES

This invention relates to a process and kit for determining the concentration of aldehydes in samples. A further aspect of the invention relates to a tablet comprising a reactant employed in the process and kit.

It is often necessary to determine whether or not the concentration of a particular chemical compound in a given medium is greater or less than a critical predetermined concentration. A specific example of where such determinations are made routinely is in the measurement of glutaraldehyde levels in glutaraldehyde-containing disinfectant solutions. The efficacy of these disinfectant solutions is in large part dependent upon the concentration of glutaraldehyde, and therefore, it is necessary to determine whether glutaraldehyde is present in an amount equal to, or greater than, its minimum effective concentration (i.e., that minimum concentration necessary for disinfection).

The art of detecting and determining the concentration of aldehyde in media is extensive. Numerous chemical reactions are known which transform aldehydes to specific reaction products. The reaction products formed in such chemical reactions may be analyzed quantitatively using conventional analytical techniques. Depending on the nature of the reaction product, suitable analytical techniques may include, for example, titration methods or spectrophotometric methods (i.e., where the reaction product is colored). An example of a known spectrophotometric assay for aldehydes involves employment of 4-amino-3-hydrazino-5-mercapto-1,2,4-triazole to transform the aldehyde to an intensely colored 6-mercapto-3-substituted-s-triazolo[4,3-b]-s-tetrazine derivative, e.g., see Jacobson et al, 46 Analytical Chemistry 298 (1974). Other methods for determining the concentration of aldehyde in media are described in U.S. Pat. Nos. 3,409,405 (Mohan), 3,837,809 (Chapman), 4,236,589 (King), and 4,298,569 (Read).

It would be desirable to have a method which, without the use of expensive or inconvenient analytical techniques, permits one to determine whether or not an aldehyde is present in a given medium in an amount greater than or less than a predetermined concentration.

The present invention provides a process for determining whether an aldehyde having at least one —CHO moiety is present in a sample in a concentration in excess of a predetermined minimum concentration. The method comprises the steps of:

(a) combining as a mixture a predetermined quantity of a sample containing or suspected of containing an aldehyde having at least one —CHO moiety; a first reaction system which is capable of transforming the aldehyde to at least one substantially stable first reaction product by a reaction involving the —CHO moiety, the amount of the first reaction system combined with the predetermined quantity of the sample being that which will transform completely to the first reaction product only an amount of aldehyde equal to the predetermined minimum concentration; and an effective amount of a second reaction system which is capable of transforming the aldehyde to at least one second reaction product by a reaction involving the —CHO moiety; the first reaction product and the second reaction product being of a nature that permits the second reaction product to be detected visually; the first reaction system and the second reaction system being further characterized in that the first reaction system is capable of transforming completely to the first reaction product an amount of aldehyde equal to the predetermined minimum concentration before the second reaction product is visually detectable;

(b) detecting visually any formation of the second reaction product.

The present invention also provides a novel kit for determining whether an aldehyde having at least one —CHO moiety is present in a predetermined quantity of a sample in an amount in excess of a predetermined minimum concentration. The kit comprises (a) a first reaction system which is capable of transforming the aldehyde to at least one substantially stable first reaction product by a reaction involving the —CHO moiety; (b) means for combining with the sample a predetermined amount of said first reaction system; and (c) an effective amount of a second reaction system which is capable of transforming the aldehyde to at least one second reaction product by a reaction involving the —CHO moiety. The first reaction system and the second reaction system are both of a nature that permits the second reaction product to be detected visually. The first reaction system and the second reaction system are further characterized in that, when both are combined with the predetermined quantity of the sample, the first reaction system is capable of transforming completely to the first reaction product essentially the amount of aldehyde which is equal to the predetermined minimum concentration before the second reaction product is visually detectable. The first reaction system and the second reaction system are packaged in a substantially stable form.

The present invention further provides a novel article of manufacture consisting of a tablet comprising a compound which reacts with an aldehyde to form a visually detectable reaction product by a reaction involving the —CHO moiety of the aldehyde. The compound is selected from the group consisting of 4-amino-3-hydrazino-5-mercapto-1,2,4-triazole; 5,5-dimethylcyclohexane-1,3-dione; 2-hydroxycarbazole, 2,4-dinitrophenylhydrazine; amino acids containing a primary amine functional group at the terminal position of the carbon chain opposite the carboxyl functionality; aniline derivatives containing a hydroxy substituent on the benzene ring; aniline derivatives containing an amine substituent on the benzene ring; and aniline derivatives containing a sulfonic acid substituent on the benzene ring. The tablet is useful as the source of a reactant for the second reaction system in the above-described process and kit. The tablet may further comprise additional ingredients which control dissolution of the reactant in the reaction medium.

The present invention provides a convenient and economical process and kit for determining whether or not an aldehyde is present in a given medium in a concentration greater than or less than a predetermined concentration without requiring employment of inconvenient and/or expensive analytical techniques. Specifically, whether or not an aldehyde is present in a concentration greater than or less than a predetermined concentration is determined by employment of two reaction systems which are capable of transforming the aldehyde into two different reaction products. The two reaction systems would normally act on the aldehyde simultaneously, but they have been formulated in such a manner that all of the first reaction system has substantially acted before the second reaction system has acted to any significant extent. The amount of the first reaction system added to the sample must be quantitated so that it reacts completely with the predetermined minimum concentration of aldehyde in the sample. The second reaction system acts only if aldehyde remains after the first reaction system has reacted completely. The reaction products of the two reaction systems are such that formation of a significant amount of the reaction product or products of the second reaction system can be observed visually either due to the formation of a distinguishable colored compound or a precipitate. The process and kit of the present invention are convenient to use since the user need only combine a sample of the aldehyde-containing sample with the reactants required by the two reaction systems.

The essentially sequential timing of the action of the two reaction systems can be achieved by a variety of means. If the reaction kinetics of the two reaction systems are such that the first reaction system acts first and goes to completion before the second reaction system has acted to any significant extent, the two reaction systems may be combined simultaneously with the sample at the beginning of the assay. If the reaction rates of the two reaction systems are essentially the same, the desired sequential timing of the two reaction systems is achieved by providing the reactant or reactants of the second reaction system in a form which slows release of the second reaction system into the reaction medium until the first reaction system has acted completely. For example, it is believed that the reactant for the second reaction system may be microencapsulated or provided with a coating in order to delay dissolution of that reactant in the reaction medium. In the preferred embodiment, a reactant for the second reaction system is provided in tablet form in order to delay the dissolution of that reactant in the reaction medium.

DESCRIPTION OF THE DRAWINGS

The present invention will be more easily understood by reference to the following drawings in which:

FIG. 1 is a cross-sectional view of one kit in accordance with the present invention;

FIG. 2 is a cross-sectional view of an alternative kit in accordance with the present invention; and FIG. 3 is a side view of still another alternative kit in accordance with the present invention.

DESCRIPTION OF THE PREFERRED EMBODIMENTS

As used in the instant specification and claims "reaction system" means and includes reactants which are involved directly in the derivatization of the aldehyde. "Reaction system" also means and includes any other reagents which faciliate such derivatization.

Suitable reactants which will form derivatives of aldehydes by a reaction involving the —CHO moiety are well-known in the art. Suitable reactants for the first reaction system and the second reaction system are those which react rapidly with the aldehyde to form a first reaction product and a second reaction product, respectively, which are of a nature that permits visual detection of the second reaction product. For example, formation of the second reaction product may be detected by either a color change in the reaction medium or formation of a precipitate. From the standpoint of convenience, it is desirable that formation of a visually detectable amount of the second reaction product occur within a few minutes. Preferred first and second reaction systems each comprise one reactant as a derivatizing agent which derivatizes the aldehyde to form the first and second reaction products, respectively.

While it is contemplated that the process of the invention may be conducted at elevated temperatures which are achieved, for example, using a heated water bath, it is preferred that the first and second reaction systems be of a nature that the process can be conducted at ambient temperatures (i.e., room temperatures). It is understood that when the assay is conducted at elevated temperatures, the reaction systems must be of such a nature that the desired delay in formation of the second reaction product is still achieved.

Reactants which generally form colorless or nearly colorless (e.g., pale yellow) derivatives of aldehydes and which are, therefore, particularly suitable for use in the first reaction system include the following: hydroxylamines, e.g., hydroxylamine-hydrochloride, which form an oxime as the first reaction product; alkoxyamines e.g., methoxyamine-hydrochloride, which form an alkoxyimine as the first reaction product; hydrazines, e.g., hydrazine dihydrochloride and substituted hydrazines such as phenylhydrazine, which form a hydrazone or a substituted hydrazone as the first reaction product; semicarbazides, e.g., semicarbazide-hydrochloride, which form a semicarbazone as the first reaction product; and azides, e.g., sodium azide and potassium azide, which form an azidoaldehyde as the first reaction product.

The reactant in the first reaction system is employed in a predetermined amount which is that amount which under the reaction conditions employed (e.g., conditions of pH, etc.) will transform to the first reaction product only the amount of aldehyde equal to the predetermined minimum concentration of the aldehyde in the quantity of the sample being assayed.

Reactants which are particularly suitable for use in the second reaction system since they form derivatives (of aldehydes) which are visually distinguishable from the above-described types of first reaction products are also well known in the art. Examples of suitable reactants for the second reaction system include the following: 4-amino-3-hydrazino-5-mercapto-1,2,4-triazole (e.g., that available commerically under the trade designation "Purpald" from Aldrich Chemical Co.) which forms a 6-mercapto-3-substituted-s-triazolo[4,3-b]-s-tetrazine as the second reaction product; 5,5-dimethylcyclohexane-1,3-dione; 2-hydroxycarbazole; certain phenyl-substituted hydrazines such as 2,4-dinitrophenyl hydrazine; amino acids such as lysine and glycine which comprise a primary amine functional group at the terminal position of the carbon chain opposite the carboxyl funcationality, such amino acids forming N-substituted imines of the respective amino acids; and aniline derivatives containing a hydroxyl substituent on the benzene ring and/or an additional amine substituent on the benzene ring and/or a sulfonic acid substituent on the benzene ring. Examples of suitable aniline derivatives include the following: 4-hydroxy-3-methoxybenzyl amine; 2,4-diaminophenol dihydrochloride; 1,2-dianiloethane; and 2,4-diaminobenzene sulfonic acid. Depending on the reaction conditions (e.g., conditions of pH), the above specifically-named aniline derivatives may result in the formation of a visually detectable precipitate. If one is assaying for a dialdehyde such as glutaraldehyde, use of one of the above specifically-named aniline derivatives as the reactant for the second reaction system is especially desirable since such derivatives are generally specific for dialdehydes. Specificity for dialdehydes may depend on the pH of the reaction medium. For example, it has been found that 2,4-diaminophenol dihydrochloride readily derivatizes both glyoxal and glutaraldehyde at a pH of about 7, but derivatizes glutaraldehyde preferentially at a pH of about 5.

The reactant for use in the second reaction system is employed in an effective amount which is that amount sufficient to assure that a visually detectable amount of the second reaction product can be formed if the aldehyde is present in excess of the predetermined minimum concentration.

Depending on the nature of the second reaction system, formation of the second reaction product may be dependent on an oxidation reaction. In such cases, at least one of the first reaction system and second reaction system may include a suitable oxidizing agent. Alternatively, a suitable oxidizing agent may simply be oxygen gas which is present in an air space above the reaction medium. Where oxygen gas is employed as the oxidizing agent, the kits of the invention need not contain oxygen gas. An example where an oxidation step is involved in the formation of the second reaction product is in the reaction of 4-amino-3-hydrazino-5-mercapto-1,2,4-triazole with an aldehyde to form a 6-mercapto-3-substituted-5-triazole[4,3-b]-s-tetrazine.

A first reaction system and a second reaction system comprising the above-described reactants generally exhibit similar reaction rates and, therefore, the second reaction system must be employed in a form which allows substantially all of the first reaction system to act completely before the second reaction system has acted to form a visually detectable amount of the second reaction product or products.

A preferred form employed for delaying the action of the second reaction system is a tablet which comprises a reactant of the second reaction system. As used in the instant specification and claims, "tablet" designates a compressed form of a powdered or particulate material. In order to facilitate tablet formation, it is preferred that the reactant selected be a solid at 22° C. A tablet comprising such a reactant may contain only that reactant in which case release of the reactant into the reaction medium is controlled by amount of compression used to formulate the tablet. Alternatively, the tablet may also include other ingredients as fillers in order to provide, for example, desired dissolution characteristics. For example, where the reaction medium is acidic in nature, inclusion of basic compounds such as phthalimide or zinc oxalate in the tablet generally impedes rapid dissolution of the reactant or reactants which are contained in the tablet. Also, inclusion of compounds such as zinc carbonate which liberate gas on contact with an acidic aqueous reaction medium generally facilitate rapid dissolution of the reactant or reactants. Where the reaction medium is alkaline in nature, inclusion of acidic compounds such as uric acid, succinic acid or benzoic acid or materials such as silica generally impedes rapid dissolution of the reactant or reactants. A suitable amount of such fillers for inclusion in a tablet is about 10 to 1000 parts by weight per 100 parts by weight of the reactant or reactants contained in the tablet.

Other ingredients which may be included in the tablet include conventional release agents such as calcium stearate which are included in order to facilitate the tablet-making process. A suitable amount of such a release agent for inclusion in a tablet is about 1 to 3 parts by weight per 100 parts by weight of the reactant or reactants contained in the tablet.

It may be desirable to form a layered tablet in which a layer comprising the reactant for the second reaction system is sandwiched between two layers of a material such as phthalimide which reduces the amount of the reactant which is exposed at the surface of the tablet. This reduces the extent to which the reactant dissolves instantaneously in the reaction medium.

The tablet may be made by conventional means. Generally, a homogeneous mixture of the reactant or reactants and any filler to be included in the tablets is prepared. Employment of a suitable solvent such as distilled water may be desirable in preparing a homogeneous mixture which can be granulated to faciliate tablet making. If desired, a release agent such as calcium stearate is then mixed into the resulting dry, homogeneous mixture. Tablets are then prepared using conventional apparatus such as an automated apparatus or a manual apparatus. The weight of the tablet may vary depending on desired results. It has been found in the present invention that a tablet weighing from about 40 to 100 milligrams is particularly suitable.

It may be important that the pH of the reaction mixture which comprises the first reaction system and the second reaction system be closely controlled. Specifically, a particular pH or pH range may be desirable in order to optimize the reaction conditions for the first reaction system and/or the second reaction system or to assure stability of the first reaction product. One or both of the reaction systems may proceed only under certain conditions of pH due to the nature of the chemical reactions involved therein. Also, the equilibrium point associated with the first reaction system may be significantly affected by pH. As a result, the amount of the reactant or reactants employed in the first reaction system may depend on the pH of the reaction medium. Further, the reactants involved in one or both of the reaction systems may be sufficiently soluble in the reaction medium only under certain conditions of pH. Finally, as discussed hereinabove, certain conditions of pH may provide desired dissolution characteristics of the reactant or reactants contained in a tablet which has been employed to delay the reaction of the second reaction system. Optimization of pH for any particular combination of reaction systems may be determined empirically and is well within the ordinary level of skill in the art.

As to the stability of the first reaction product, it is important that the first reaction product be stable for the period of time required for the assay to be completed (generally thirty seconds to several minutes depending on the formation time of the second reaction product). If the first reaction product is substantially unstable during such a time frame, a significant amount of aldehyde which should have been consumed by the first reaction system in forming the first reaction product may be regenerated and will be available for transformation to the second reaction product. The consequence of this may be an erroneous assay.

Where the pH of the reaction medium is an important parameter and addition of an acid or base is required in order to provide the desired conditions of pH, such an acid or base may be included in the first reaction system and/or second reaction system. It is preferred that the acid or base be employed in the form of an aqueous solution. Where an acid or base is included in the first reaction system and/or the second reaction system, it is to be understood that such is not a "reactant" for the first reaction system and/or second reaction system as that term is used in the instant specification and claims.

A preferred process and kit in accordance with the present invention employ an aqueous solution of hydroxylamine-hydrochloride as the reactant for the first reaction system and 4-amino-3-hydrazino-5-mercapto-1,2,4-triazole as the reactant for the second reaction system. The 4-amino-3-hydrazino-5-mercapto-1,2,4-triazole is employed in the form of a tablet which comprises 3 parts by weight of 4-amino-3-hydrazino-5-mercapto-1,2,4-triazole and 1 part by weight of benzoic acid. In order to facilitate dissolution of the 4-amino-3-hydrazino-5-mercapto-1,2,4-triazole in the reaction medium and provide suitable conditions for the formation of the first reaction product, aqueous sodium hydroxide is employed.

Generally, first reaction systems and second reaction systems which exhibit substantially equivalent reaction rates are maintained separately until the time that an assay is to be conducted. As indicated hereinabove, the first reaction system may have associated therewith an equilibrium point which is affected significantly by pH. Accordingly, the order in which the various reactants of the two reaction systems and the sample to be assayed are combined may dictate the amount or amounts of the reactant or reactants for the first reaction system which need be employed. Thus, the appropriate amounts of each reaction system must be determined empirically with regard to all reaction conditions.

The first reaction system and the second reaction system should be packaged in a manner which assures that the two reaction systems are substantially stable (i.e., exhibit a shelf-life of at least about 2 months at room temperature).

Kits comprising the first reaction system and second reaction system may assume a variety of convenient forms. For example, the kit illustrated in FIG. 1 may consist of a plurality of sealable, deformable plastic reaction containers 10 which each contain a tablet 11 comprising a reactant for the second reaction system and a breakable ampule (e.g., a crushable glass ampule) 12 containing a solution 13 of a reactant for the first reaction system. Cap 14 seals the reaction container 10 where an acid or base is included in order to provide desired conditions of pH and that acid or base is compatible with the reactant for the first reaction system, the acid or base may be included in the glass ampule. Also, it may be desirable for the ampule to contain an inert atmosphere (e.g., nitrogen gas). Each reaction system is present in each reaction container in an amount appropriate for assaying for a particular minimum concentration of an aldehyde in a sample using a predetermined quantity of the sample. In use, the predetermined quantity of the sample is added to the reaction container and the reaction container is sealed. The ampule is then crushed by squeezing the wall of the plastic reaction container such that the tablet, the contents of the ampule, and the sample are combined together. The reaction container is shaken for several minutes to assure complete mixing and to facilitate dissolution of the reactant which is contained in the tablet. An example of a suitable reaction container and ampule is that disclosed in U.S. Pat. No. 3,661,717 (Nelson), incorporated herein by reference. For purposes of the present invention, it is preferred that the cap for the reaction container be such that it seals completely the reaction container (i.e., comprises no aperture).

In another embodiment (FIG. 2), the kit comprises a plurality of plastic pipettes 20 having a long hollow stem portion 21 which is open at one end 22 and an enclosed enlarged portion 23 situated adjacent to and connected to the stem portion. The pipette is adapted to draw therein a fixed quantity of the sample being assayed. A suitable pipette is that disclosed in U.S. Des. Pat. No. 250,599, incorporated herein by reference. Within the enlarged portion of the pipette is included a tablet 24 comprising a reactant for the second reaction system and a breakable ampule 25 which contains a solution 26 containing a reactant for the first reaction system and any acid or base which is included to provide desired conditions of pH and which is compatible with that reactant. In use, a fixed quantity of the sample being assayed is drawn into the pipette through its open stem. The pipette is then inverted such that the stem of the pipette is pointing substantially upwardly and the sample passes completely to the enlarged portion. The ampule is then crushed by squeezing the wall of the enlarged portion of the pipette. The pipette is shaken in that position for several minutes to assure complete mixing and to facilitate dissolution of the reactant which is contained in the tablet.

A preferred kit (FIG. 3) in accordance with the present invention comprises a plurality of disposable reaction containers 30; an aqueous solution of the reactant for the first reaction system which is contained in a suitable container 31 and which is present in an amount sufficient for a plurality of assays; a plurality of tablets 33 comprising the reactant for the second reaction system; and an aqueous acidic or basic solution if such is necessary or desirable to provide particular conditions of pH. One or more pipettes 34 having fixed delivery volumes may be included in the kit to permit convenient measurement of appropriate volumes of the aqueous components of the kit and the sample.

The examples shown below are merely illustrative and are not to be construed as a limitation of the invention. Other variations, substitutions and changes in the ingredients and parameters may be made without departing from the scope of the invention.

TEST METHOD

Quantitation of Glutaraldehyde in Aqueous Samples

Glutaraldehyde was quantitated in several of the following examples as follows:

A 0.5 N alcoholic solution of hydroxylaminehydrochloride was prepared by dissolving 35 grams of hydroxylamine-hydrochloride in 150 ml of distilled water and diluting to 1000 ml with anhydrous isopropyl alcohol.

A 0.5 N aqueous solution of triethanolamine was prepared by diluting 65 ml (74 grams) of 98% triethanolamine to 1000 ml with distilled water.

Fifteen ml of a 0.04% alcoholic solution of bromophenol blue indicator was added to the above hydroxylamine-hydrochloride solution. From a buret was then added 0.5 N triethanolamine until the solution appeared greenish-blue.

To 500-ml glass-stoppered Erlenmeyer flasks was added 65 ml of the neutralized hydroxylamine-hydrochloride solution and exactly 50 ml of the 0.5 N triethanolamine solution. A weighed sample (about 10 to 20 g) to be assayed was added to one of the flasks, at which time the flask was purged with a stream of nitrogen for two minutes and stoppered. A suitable blank was also prepared. The flasks containing the sample and blank were allowed to stand for 60 minutes at room temperature and were swirled occasionally. The blank and sample were then titrated potentiometrically with standard 0.1 N sulfuric acid. The percent by weight of glutaraldehyde was then determined using the following calculation:

$$\frac{(B - A)N \times 5.01}{gm\ sample} = glutaraldehyde,\ \%\ by\ weight$$

where
A = ml of 0.1 N sulfuric acid required for the sample;
B = ml of 0.1 N sulfuric acid required for the blank; and
N = the normality of the sulfuric acid solution used.

EXAMPLE I

This example describes a process whereby it was confirmed that a glutaraldehyde-containing solution contained glutaraldehyde in an amount in excess of 1% by weight. The glutaraldehyde-containing solution was known via the above-described Test Method to contain glutaraldehyde in an amount of 1.07% by weight.

The reactant for the quantitative first reaction was a 0.2649 milliequivalent per milliliter aqueous hydroxylamine-hydrochloride solution. This solution was prepared by weighing 18.40 grams of reagent grade hydroxylamine-hydrochloride and mixing it with deionized water to give a final volume of one liter.

The reactant for the second reaction system was 4-amino-3-hydrazino-5-mercapto-1,2,4-triazole (e.g., that commercially available under the trade designation "Purpald" from Aldrich Chemical Co.) which was in the form of a tablet which comprised one part by weight of benzoic acid, three parts by weight of the 4-amino-3-hydrazino-5-mercapto-1,2,4-triazole, and 0.04 parts by weight of calcium stearate. The tablet was obtained by preparing, using a Hobart Mixer, Model AS 200 DT (Hobart Company), a homogeneous mixture of one part by weight benzoic acid, three parts by weight of 4-amino-3-hydrazino-5-mercapto-1,2,4-triazole and one part by weight of distilled water. The resulting mixture was placed for 30 minutes on a Model "STPKE2" fluid-bed drier (available from Aeromatic AG) which was operated at 30° C. The resulting crusty material was then granulated using a "Wet Granulator" oscillator having a 14-mesh screen (available form Erweke). A mixture comprising 99 parts by weight of the granulated material and 1 part by weight of calcium stearate was prepared. A 50 milligram tablet was prepared from the mixture using a "Stokes B2 Rotary Tablet Machine" (available from Pennwalt Corporation) having 3/16-inch (0.48 cm) tooling and operated at 2000 lbs (907 kg) compression pressure.

The last component required for this process was a 4.5 molar aqueous sodium hydroxide solution.

A one milliliter aliquot of the glutaraldehyde-containing solution was added to a 7 cc reaction container which contained one milliliter of the aqueous hydroxylamine-hydrochloride solution. One milliliter of the aqueous sodium hydroxide solution and the tablet containing the 4-amino-3-hydrazino-5-mercapto-1,2,4-triazole were added subsequently. The reaction container was closed and shaken for several minutes during which time a purple color developed which confirmed that the glutaraldehyde-containing solution contained glutaraldehyde in an amount in excess of 1% by weight.

EXAMPLE II

This example describes a process whereby it was confirmed that a glutaraldehyde-containing solution contained glutaraldehyde in an amount less than 1.3% by weight. The glutaraldehyde-containing solution was known via the above-described Test Method to contain glutaraldehyde in an amount of 1.28% by weight.

The reactant for the quantitative first reaction was a 0.347 milliequivalent per milliliter aqueous hydroxylamine-hydrochloride solution.

The reactant for the second reaction system was 4-amino-3-hydrazino-5-mercapto-1,2,4-triazole which was in the form of a tablet identical to that prepared in Example I.

The last component required for this process was a 4.5 molar aqueous sodium hydroxide solution.

A one milliliter aliquot of the glutaraldehyde-containing solution was added to a 7 cc reaction container which contained one milliliter of the aqueous hydroxylamine-hydrochloride solution. One milliliter of the aqueous sodium hydroxide solution and the tablet containing the 4-amino-3-hydrazino-5-mercapto-1,2,4-triazole were added subsequently. The reaction container was closed and shaken for several minutes during which time no purple color developed, confirming that the glutaraldehyde-containing solution contained glutaraldehyde in an amount of less than 1.3% by weight.

EXAMPLE III

This example describes an alternative process whereby it was confirmed that a glutaraldehyde-containing solution contained glutaraldehyde in an amount in excess of 1% by weight. The glutaraldehyde-containing solution was known via the above-described Test Method to contain glutaraldehyde in an amount of 1.07% by weight.

The reactant for the quantitative first reaction system was a 0.13 milliequivalent per milliliter solution of semicarbazide-hydrochloride in deionized water. This solution was prepared by weighing 14.50 grams of reagent grade semicarbazide and mixing it with deionized water to give a final volume of one liter.

The reactant for the second reaction system was 2,4-diaminophenol-dihydrochloride which was in the form of a tablet which comprised ten parts by weight of benzoic acid and one part by weight of the 2,4-diaminophenoldihydrochloride. The tablet was obtained by preparing a homogeneous mixture of the dry ingredients by simply mixing the ingredients in the above-indicated proportions. A 50 milligram tablet was prepared from the mixture using a Parr Pellet Press (Parr Instrument Co.) having a 0.118 inch (0.300 cm) punch.

A one milliliter aliquot of the glutaraldehyde-containing solution was added to a 7 cc reaction container which contained one milliliter of the aqueous semicarbazidehydrochloride solution. One tablet containing the 2,4-diaminophenol-dihydrochloride was added subsequently. The reaction container was closed and shaken for several minutes during which time a brown color developed which confirmed that the glutaraldehyde-containing solution contained glutaraldehyde in an amount in excess of 1% by weight.

EXAMPLE IV

This example describes yet another alternative process whereby it was confirmed that a glutaraldehyde-containing solution contained glutaraldehyde in an amount in excess of 0.9% by weight. The glutaraldehyde-containing solution was known via the above-described Test Method to contain glutaraldehyde in an amount of 0.92% by weight.

The reactant for the first reaction system was a 0.2 molar aqueous hydrazine-dihydrochloride solution. The solution was prepared by weighing 20.996 grams of reagent grade hydrazine-dihydrochloride and mixing it with deionized water to give a final volume of one liter.

The reactant for the second reaction system was 4-amino-3-hydrazino-5-mercapto-1,2,4-triazole which was in the form of a tablet identical to that prepared in Example I.

The last component required for this process was a 4.5 molar aqueous sodium hydroxide solution.

A 0.2 milliliter aliquot of the glutaraldehyde-containing solution is added to a 7 cc reaction container which contained 1.6 milliliters of the hydrazinedihydrochloride solution. One milliliter of the aqueous sodium hydroxide solution and the tablet containing the 4-amino-3-hydrazino-5-mercapto-1,2,4-triazole were added subsequently. The reaction container was closed and shaken for several minutes, during which time a purple color developed which confirmed that the glutaraldehyde-containing solution contained glutaraldehyde in an amount in excess of 0.9% by weight.

EXAMPLE V

This example describes yet another alternate process whereby it was confirmed that a glutaraldehyde-containing solution contained glutaraldehyde in an amount in excess of 0.9% by weight. The glutaraldehyde containing solution was known via the above-described Test Method to contain glutaraldehyde in an amount of 0.92 % by weight.

The reactant for the quantitative first reaction system was a 0.05 molar aqueous potassium azide solution. The solution was prepared by weighing 5.249 grams of reagent grade potassium azide and mixing it with deionized water to give a final volume of one liter.

The reactant for the second reaction system was 2,4-diaminophenol-dihydrochloride which was in the form of a 50 milligram tablet which comprised one part by weight phthalimide, one part by weight of the 2,4-diaminophenoldihydrochloride and 0.1 parts by weight of "Aerosil OX50" (a pyrogenic silica commercially available from DeGussa, Inc.). The tablet was prepared in accordance with the procedure of Example III with all the ingredients being combined at once to provide a homogeneous mixture from which the tablet was made.

The last component required for this process was a 3 molar aqueous hydrochloric acid solution.

A 0.1 milliliter aliquot of the glutaraldehyde-containing solution was added to a 7 cc reaction container which contained 2.0 milliliter of the potassium azide solution. One milliliter of the aqueous hydrochloric acid solution and the tablet containing the 2,4-diaminophenoldihydrochloride were added subsequently. The reaction container was closed and shaken for several minutes, during which time a brown color developed which confirmed that the glutaraldehyde-containing solution contained glutaraldehyde in an amount in excess of 0.9% by weight.

EXAMPLE VI

This example describes yet another alternative process whereby it was confirmed that a glutaraldehyde-containing solution contained glutaraldehyde in an amount in excess of 0.9% by weight. The glutaraldehyde-containing solution was known via the above-described Test Method to contain glutaraldehyde in an amount of 0.92% by weight.

The reactant for the quantitative first reaction system was a 0.05 molar aqueous methoxyamine-hydrochloride solution. The solution was prepared by weighing 4.176 grams of reagent grade methoxyamine-hydrochloride and mixing it with deionized water to give a final volume of one liter.

The reactant for the second reaction system was 4-amino-3-hydrazino-5-mercapto-1,2,4-triazole which was in the form of a tablet identical to that prepared in Example I.

The last component required for this process was a 4.5 molar aqueous sodium hydroxide solution.

A 0.2 milliliter aliquot of the glutaraldehyde-containing solution was added to a 7 cc reaction container which contained 1.0 milliliter of methoxyaminehydrochloride solution. One milliliter of the aqueous sodium hydroxide solution and the tablet containing the 4-amino-3-hydrazino-5-mercapto-1,2,4-triazole were added subsequently. The reaction container was closed and shaken for several minutes, during which time a purple color developed which confirmed that the glutaraldehyde-containing solution contained glutaraldehyde in an amount in excess of 0.9% by weight.

EXAMPLE VII

This example describes yet another alternative process whereby it was confirmed that a glutaraldehyde-containing solution contained glutaraldehyde in an amount in excess of 0.9% by weight. The glutaraldehyde-containing solution was known via the above-described Test Method to contain glutaraldehyde in an amount of 0.92% by weight.

The reactant for the quantitative first reaction system was a 0.05 molar aqueous hydrazine-dihydrochloride solution. The solution was prepared by in accordance with the procedure of Example V.

The reactant for the second reaction system was 4-hydroxy-3-methoxybenzylamine which was in the form of a 50 milligram tablet which comprised one part by weight of zinc carbonate and one part by weight of the 4-hydroxy-3-methoxybenzylamine. The tablet was prepared in accordance with the procedure of Example III.

The last component required for this process was a 3 molar aqueous hydrochloric acid solution.

A one milliliter aliquot of the glutaraldehyde-containing solution was added to a 7 cc reaction container which contained 0.5 milliliter of the hydrazine-dihydrochloride solution. Two-tenths of a milliliter of the hydrochloric acid solution and the tablet containing the 4-hydroxy-3-methoxybenzylamine were added subsequently. The reaction container was closed and shaken for several minutes, during which time a yellow-brown color developed which confirmed that the glutaraldehyde-containing solution contained glutaraldehyde in an amount in excess of 0.9% by weight.

EXAMPLE VIII

This example describes a process whereby it was confirmed that a formaldehyde-containing solution contained formaldehyde in an amount in excess of 1% by weight. The formaldehyde-containing solution was prepared by diluting a commercially available formaldehyde-containing solution of known formaldehyde content and was known to contain formaldehyde in an amount of 1.1% by weight.

The reactant for the first reaction system was a 0.21 molar aqueous hydroxylamine-hydrochloride solution. This solution was prepared by weighing 14.73 grams of hydroxylamine-hydrochloride and mixing it with deionized water to give a final volume of one liter.

The reactant for the second reaction system was 4-amino-3-hydrazino-5-mercapto-1,2,4-triazole which was in the form of a tablet identical to that prepared in Example I.

The last component required for this process was a 4.5 molar aqueous sodium hydroxide solution.

A 0.8 milliliter aliquot of the formaldehyde-containing solution was added to a 7 cc reaction container which contained 1 milliter of the hydroxylamine-hydrochloride solution. One milliliter of the aqueous sodium hydroxide solution and the tablet containing the 4-amino-3-hydrazino-5-mercapto-1,2,4-triazole were added subsequently. The reaction container was closed and shaken for several minutes, during which time a violet color developed which confirmed that the formaldehyde-containing solution contained formaldehyde in an amount in exess of 1% by weight.

EXAMPLE IX

This example describes a process whereby it was confirmed that a p-dimethylaminobenzaldehyde-containing solution contained p-dimethylaminobenzaldehyde in an amount in excess of 1.4% by weight. The p-dimethylaminobenzaldehyde-containing solution was prepared to contain p-dimethylaminobenzaldehyde in an amount of 1.5% by weight.

The reactant for the quantatative first reaction was a 0.21 aqueous hydroxylamine-hydrochloride solution. This solution was prepared by in accordance with the procedure of Example VIII.

The reactant for the second reaction system was 2,4-diaminobenzene sulfonic acid which was in the form of a 50 milligram layered tablet, the lower layer of which accounted for about 10 milligrams of the total tablet weight and comprised phthalimide, a middle layer of which accounted for about 30 milligrams of the total tablet weight and comprised one part by weight of phthalimide, one part by weight of 2,4-diaminobenzene sulfonic acid, and 0.1 part by weight of submicron silica, and the top layer of which comprised about 10 milligrams of phthalimide. This tablet was prepared using a Parr Pellet Press (Parr Instrument Co.) by first forming a pellet comprising the lower layer and then adding successively the middle and outer layers.

The last component required for this process was a 3 molar aqueous hydrochloric acid solution.

A 0.2 milliliter aliquot of the p-dimethylaminobenzaldehyde-containing solution was added to a 7 cc reaction container which contained 0.2 milliliter of the aqueous hydroxylamine hydrochloride solution. Two-tenths of a milliliter of the aqueous hydrochloric acid solution and the tablet containing the 2,4-diaminobenzene sulfonic acid were added subsequently. The reaction container was closed and shaken for several minutes, during which time an orange precipitate formed which confirmed that the p dimethylaminobenzaldehyde-containing solution contained p-dimethylaminobenzaldehyde in an amount in excess of 1.5% by weight.

What is claimed is:

1. A process for determining whether an aldehyde having at least one —CHO moiety is present in a sample in a concentration in excess of a predetermined minimum concentration, comprising the steps of:
    (a) combining as a mixture:
        (1) a predetermined quantity of said sample;
        (2) a first reaction system which is capable of transforming said aldehyde to at least one substantially stable first reaction product by a reaction involving said —CHO moiety, the amount of said first reaction system combined with said predetermined quantity of said sample being that which will transform completely to said first reaction product only an amount of aldehyde equal to said minimum concentration of aldehyde in said predetermined quantity of said sample; and
        (3) an effective amount of a second reaction system which is capable of transforming said aldehyde to at least one second reaction product by a reaction involving said —CHO moiety; said first reaction product and said second reaction product both being of a nature that permits said second reaction product to be detected visually in the presence of said first reaction product without interference therefrom;
    said first reaction system and said second reaction system being further characterized in that said first reaction system transforms substantially all of said amount of aldehyde equal to said predetermined minimum concentration to said first reaction product before said second reaction product is visually detectable; and
    (b) detecting visually any formation of said second reaction product.

2. A process in accordance with claim 1, wherein said first reaction product is substantially colorless.

3. A process in accordance with claim 2, wherein said first reaction system comprises a reactant selected from the group consisting of hydroxylamine, hydroxylamine salts, hydrazine, hydrazine salts, substituted hydrazines, semicarbazide, semicarbazide salts, sodium azide and potassium azide and said reactant of said second reaction system is in tablet form and selected from the group consisting of 4-amino-3-hydrazino-5-mercapto-1,2,4-triazole, 5,5-dimethylcyclohexane-1,3-dione, 2-hydroxycarbazole, 2,4-dinitrophenyl hydrazine, amino acids containing a primary amine functional group at the terminal position of the carbon chain opposite the carboxyl functionality, aniline derivatives containing a hydroxy substituent on the benzene ring, aniline derivatives containing an amine substituent on the benzene ring, and aniline derivatives containing a sulfonic acid substituent on the benzene ring.

4. A process in accordance with claim 1, wherein said second reaction system comprises a reactant which is in tablet form.

5. A process in accordance with claim 1, wherein said first reaction system and said second reaction system are capable of acting on said aldehyde at ambient temperature and said process is conducted at ambient temperature.

6. A process in accordance with claim 1, wherein said mixture includes water.

7. A process for determining whether an aldehyde having at least one —CHO moiety is present in a sample in a concentration in excess of a predetermined minimum concentration, comprising the steps of:
(a) combining as a mixture:
(1) a predetermined portion of said sample;
(2) a first reaction system which is capable of transforming said aldehyde to at least one substantially stable first reaction product by a reaction at ambient temperature involving said —CHO moiety, said first reaction system being combined in an amount which will convert substantially completely to said first reaction product only the amount of said aldehyde equal to said minimum concentration of aldehyde in said predetermined quantity of said sample; and
(3) an effective amount of a second reaction system which is capable of transforming said aldehyde to at least one second reaction product by a reaction at ambient temperature involving said —CHO moiety; said first reaction product and said second reaction product both being of a nature that permits formation of said second reaction product to be detected visually in the presence of said first reaction product without interference therefrom; said second reaction system being characterized in that at least one reactant of said second reaction system is in tablet form and said first reaction system is capable of transforming completely to said first reaction product substantially the amount of aldehyde equal to said predetermined minimum concentration before said second reaction product is visually detectable; and
(b) detecting visually any formation of said second reaction product.

8. A process in accordance with claim 7, wherein said first reaction product is substantially colorless.

9. A process in accordance with claim 8, wherein said first rection system comprises a hydroxylamine salt and said second reaction system comprises 4-amino-3-hydrazino-5-mercapto-1,2,4-triazole in said tablet form.

10. A process in accordance with claim 9, wherein at least one of said first reaction system and second reaction system comprises an aqueous base to facilitate dissolution of said 4-amino-3-hydrazino-5-mercapto-1,2,4-triazole.

11. A process in accordance with claim 7, wherein said tablet further comprises filler in an amount of about 10 to 1000 parts by weight per 100 parts by weight of said reactant.

12. A process in accordance with claim 9, wherein said tablet further comprises filler in an amount of about 10 to 1000 parts by weight per 100 parts by weight of said reactant.

13. A process in accordance with claim 12, wherein said filler is benzoic acid.

14. A kit for determining whether an aldehyde having at least one —CHO moiety is present in a predetermined quantity of a sample in an amount in excess of a predetermined minimum concentration, comprising (a) a first reaction system which is capable of transforming said aldehyde to at least one substantially stable first reaction product by a reaction involving said —CHO moiety; (b) means for combining with said sample a predetermined amount of said first reaction system; and (c) an effective amount of a second reaction system which is capable of transforming said aldehyde to a second reaction product by a reaction involving said —CHO moiety; said first reaction system and said second reaction system both being of a nature that permits formation of said second reaction product to be detected visually in the presence of said first reaction product without interference therefrom; said first reaction system and said second reaction system being further characterized in that when both are combined with said predetermined quantity of said sample said first reaction system transforms substantially all of said aldehyde equal to said predetermined minimum concentration to said first reaction product before said second reaction product is visually detectable; said first reaction system and said second reaction system being packaged in a substantially stable form.

15. A kit for determining whether an aldehyde having at least one —CHO moiety is present in a predetermined quantity of a sample in an amount in excess of a predetermined minimum concentration, comprising (a) a first reaction system which is capable of transforming said aldehyde to at least one substantially stable first reaction product by a reaction at ambient temperature involving said —CHO moiety; (b) means for combining with said sample a predetermined amount of said first reaction systems; and (c) an effective amount of a second reaction system which is capable of transforming said aldehyde to a second reaction product by a reaction at ambient temperature involving said —CHO moiety; said second reaction system being further characterized in that a reactant of said second reaction system is in tablet form such that when said first reaction system, said second reaction system and said predetermined quantity of said sample are combined, said first reaction system transforms substantially all of said aldehyde equal to said predetermined minimum concentration to said first reaction product before said second reaction product is visually detectable; said second reaction product being visually detectable in the presence of said first reaction product without interference therefrom; said first reaction system and said second reaction system being packaged in a substantially stable form.

16. A kit in accordance with claim 15, wherein said first reaction system comprises a reactant which results in the formation of a substantially colorless first reaction product and is selected from the group consisting of hydroxylamine, hydroxylamine salts, hydrazine, hydrazine salts, substituted hydrazines, substituted hydrazine salts, semicarbazide, semicarbazide salts, sodium azide, and potassium azide and said reactant of said second reaction system which is in tablet form is selected from the group consisting of 4-amino-3-hydrazino-5-mercapto-1,2,4-triazole, 5,5-dimethylcyclohexane-1,3-dione, 2-hydroxycarbazole, 2,4-dinitrophenylhydrazine, amino acids containing a primary amine functional group at the terminal position of the carbon chain opposite the carboxyl functionality, aniline derivatives containing a hydroxy substituent on the benzene ring, aniline derivatives containing an amine substituent on the benzene ring, and aniline derivatives containing a sulfonic acid substituent on the benzene ring.

17. A kit in accordance with claim 15, wherein said first reaction system comprises an aqueous solution of a hydroxylamine salt and said second reaction system comprises 4-amino-3-hydrazino-5-mercapto-1,2,4-triazole in said tablet form.

18. A kit in accordance with claim 17, wherein said tablet further comprises a filler in an amount of about 10-1000 parts by weight per 100 parts by weight of said 4-amino-3-hydrazino-5-mercapto-1,2,4-triazole.

19. A kit in accordance with claim 18, wherein said filler is benzoic acid.

20. A kit in accordance with claim 15, wherein one of said first reaction system and said second reaction system includes an aqueous base.

21. A kit in accordance with claim 15, said kit comprising a reaction container; an aqueous solution comprising the first reaction system and contained in a second container; and a tablet comprising at least one reactant of the second reaction system.

22. A kit in accordance with claim 15, said kit comprising a sealable, deformable plastic reaction container comprising (a) a tablet which comprises at least one reactant of the second reaction system and (b) a breakable ampule which comprises an aqueous solution comprising the first reaction system.

23. A kit in accordance with claim 15, said kit comprising a plastic pipette having a long hollow stem portion which is open at one end and an enclosed enlarged portion situated adjacent to and connected to said stem portion, said enclosed enlarged portion containing a tablet which comprises at least one reactant of the second reaction system and a breakable ampule which comprises an aqueous solution comprising the first reaction system.

* * * * *